(12) United States Patent
Glaug et al.

(10) Patent No.: US 9,132,046 B2
(45) Date of Patent: Sep. 15, 2015

(54) ABSORBENT CORE AND DISPOSABLE ABSORBENT PRODUCT WITH SUCH ABSORBENT CORE

(75) Inventors: Frank Steven Glaug, Chester Springs, PA (US); Joshua Daniel Carney, Gothenburg (SE); Sue Uner, Folsom, PA (US)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 494 days.

(21) Appl. No.: 13/336,684

(22) Filed: Dec. 23, 2011

(65) Prior Publication Data

US 2013/0165886 A1 Jun. 27, 2013

(51) Int. Cl.
| | |
|---|---|
| A61F 13/15 | (2006.01) |
| A61F 13/494 | (2006.01) |
| A61F 13/45 | (2006.01) |
| A61F 13/472 | (2006.01) |
| A61F 13/49 | (2006.01) |

(52) U.S. Cl.
CPC ............. *A61F 13/4946* (2013.01); *A61F 13/45* (2013.01); *A61F 13/47236* (2013.01); *A61F 2013/4568* (2013.01); *A61F 2013/4908* (2013.01); *A61F 2013/49068* (2013.01); *A61F 2013/49074* (2013.01); *A61F 2013/49082* (2013.01)

(58) Field of Classification Search
CPC ....... A61F 13/45; A61F 13/47; A61F 13/472; A61F 13/47236; A61F 13/00021; A61F 2013/49068; A61F 2013/49074; A61F 2013/49076; A61F 2013/49077; A61F 2013/49079; A61F 2013/4908; A61F 2013/49082; A61F 13/47245

USPC ......... 604/385.01, 304, 307, 308; 602/41, 56; D24/124–126
See application file for complete search history.

(56) References Cited

U.S. PATENT DOCUMENTS 2,890,700 A * 6/1959 Lonberg-Holm ............. 604/364
4,610,682 A * 9/1986 Kopp ....................... 604/385.21
(Continued)

FOREIGN PATENT DOCUMENTS

EP        0 172 036      2/1986
FR        2590125 A1    5/1987
(Continued)

OTHER PUBLICATIONS

Notification of Transmittal and the International Preliminary Examination Report on Patentability (Forms PCT/IPEA/416 and PCT/IPEA/409) issued on Jan. 31, 2014, by the International Bureau of WIPO in corresponding International Application No. PCT/EP2012/076139. (12 pages).

(Continued)

*Primary Examiner* — Lynne Anderson
*Assistant Examiner* — Bradley Philips
(74) *Attorney, Agent, or Firm* — Buchanan Ingersoll & Rooney P.C.

(57) ABSTRACT

A disposable absorbent product extends along a longitudinal dimension and a width dimension. The absorbent product has a backsheet, a topsheet overlaying the backsheet, and an absorbent core disposed between the backsheet and the topsheet for absorbing and retaining fluid secreted by a wearer of the absorbent product. The absorbent core includes a pair of arm portions and a pair of leg portions, with the arm and leg portions protruding laterally and longitudinally from a central portion of the absorbent core.

18 Claims, 8 Drawing Sheets

(56) References Cited

U.S. PATENT DOCUMENTS

| | | | |
|---|---|---|---|
| 4,735,624 A | | 4/1988 | Mazars |
| 4,738,675 A | * | 4/1988 | Buckley et al. ............... 604/380 |
| 4,762,521 A | * | 8/1988 | Roessler et al. ......... 604/385.26 |
| 4,938,753 A | * | 7/1990 | Van Gompel et al. ... 604/385.29 |
| D345,791 S | * | 4/1994 | Middleman .................. D24/126 |
| 5,385,500 A | | 1/1995 | Schmidt |
| 5,403,303 A | | 4/1995 | Beplate |
| 5,558,659 A | * | 9/1996 | Sherrod et al. ........... 604/385.26 |
| D423,098 S | * | 4/2000 | Stancyk, Jr. .................. D24/126 |
| 6,156,951 A | * | 12/2000 | Gustafsson et al. .......... 604/369 |
| D480,144 S | * | 9/2003 | Adams et al. ................ D24/189 |
| 7,368,027 B2 | | 5/2008 | Schneider et al. |
| 2002/0193728 A1 | * | 12/2002 | Infantino et al. ................ 604/25 |
| 2006/0003658 A1 | | 1/2006 | Hall et al. |
| 2009/0204092 A1 | * | 8/2009 | Loyd et al. ............... 604/385.03 |
| 2009/0270825 A1 | * | 10/2009 | Wciorka et al. ............. 604/367 |
| 2010/0305529 A1 | * | 12/2010 | Ashton et al. ................ 604/361 |
| 2010/0318053 A1 | | 12/2010 | Smet |

FOREIGN PATENT DOCUMENTS

| | | |
|---|---|---|
| GB | 2 325 147 A | 11/1998 |
| WO | 9428840 A2 | 12/1994 |
| WO | 2005110320 A1 | 11/2005 |
| WO | 2011081206 A1 | 7/2011 |

OTHER PUBLICATIONS

Notification of Transmittal of the International Search Report and the Written Opinion of the International Searching Authority or the Declaration (Form PCT/ISA/210)/Written Opinion of the International Searching Authority (Form PCT/ISA/237) dated Mar. 8, 2013 issued in the corresponding International Patent Application No. PCT/EP2012/076139.

Written Opinion of the International Preliminary Examining Authority issued Aug. 1, 2013 in PCT/EP2012/076139.

* cited by examiner

ABSORBENT CORE AND DISPOSABLE ABSORBENT PRODUCT WITH SUCH ABSORBENT CORE

CROSS-REFERENCE TO RELATED APPLICATIONS

This application is generally related to U.S. patent application Ser. No. 13/336,731, entitled "Disposable Absorbent Product with Elastic Leg Opening Regions and Related Methods," filed on Dec. 23, 2011, and the entire contents of which are hereby expressly incorporated by reference herein.

TECHNICAL FIELD

The present invention is generally related to absorbent products and, more particularly, to disposable absorbent products that are worn by humans for the containment and absorption of fluid bodily secretions.

BACKGROUND

Disposable absorbent products for absorption of bodily fluids are available in different types, designs, and dimensions. For example, training pants, baby diapers, adult diapers, and incontinence guards are products designed for the containment of urine and excrement. There are other types of disposable absorbent articles, such as feminine hygiene products (e.g., heavy and light incontinence pads, pantiliners) that are designed to contain and absorb urine and/or menses secreted by female wearers. Known products of this type typically include a topsheet facing the body of the wearer, a backsheet facing the garment worn by the wearer, and an absorbent core sandwiched between the topsheet and backsheet.

In conventional products of the type described above, the absorbent core may have a rectangular shape, or some other shape chosen to provide sufficient absorption for the fluids secreted by the wearer. But many of those products, especially those intended to contain urine, tend to leak the secreted fluids, which leads to discomfort for the wearer and/or the caretaker. It has been observed, for example, that leakage of urine occurs as the wearer lies on his/her side, while sleeping, notably in the areas of the product that surround the legs or adjacent the groin of the wearer. Some products have also been observed to leak adjacent the back waist area of the wearer.

Accordingly, it is desirable to provide an absorbent core and disposable absorbent products containing such absorbent core, that address these and other drawbacks of conventional disposable absorbent products.

SUMMARY

In one embodiment, a disposable absorbent product is provided that extends along a longitudinal dimension and a width dimension. The absorbent product has a backsheet, a topsheet overlaying the backsheet, and an absorbent core disposed between the backsheet and the topsheet for absorbing and retaining fluid secreted by a wearer of the absorbent product. The absorbent core includes a pair of arm portions and a pair of leg portions, with the arm and leg portions protruding laterally and longitudinally from a central portion of the absorbent core.

The absorbent core may additionally include a terminal portion located centrally, in the width dimension, between the pairs of arm and leg portions and protruding longitudinally from a remainder of the absorbent core. In certain embodiments, the disposable absorbent product includes a front waist portion adapted, in use, to face the front of the wearer, and a back waist portion adapted, in use, to face the back of the wearer. In those embodiments, the leg portions of the absorbent core are located in the front waist portion, and the terminal portion of the absorbent core is located in the back waist portion. Additionally or alternatively, each of the leg portions may extend along a minor axis, with each of the minor axes being angled with respect to a longitudinal axis of the absorbent core.

In specific embodiments, the disposable absorbent product may be such that the topsheet and backsheet jointly define an interior face of the disposable absorbent product adapted to face the body of the wearer during use, and an exterior face thereof adapted to face away from the wearer during use. The interior face in those embodiments has a total surface area, and the absorbent core occupies a surface area equal to or greater than about 50% of the total surface area of said interior face. The absorbent core may further include a concave terminal edge extending between the leg portions and/or a pair of concave lateral edges, each extending between one of the arm portions and one of the leg portions. Each of the lateral edges may, additionally or alternatively, be shaped so as to generally match the shape of an adjacent one of the leg openings.

In another embodiment, a disposable absorbent product is provided that extends along a longitudinal dimension and a width dimension. The absorbent product has a backsheet, and a topsheet overlaying the backsheet, with the topsheet and backsheet jointly defining an interior face of the disposable absorbent product adapted to face the body of the wearer during use. An exterior face of the disposable absorbent product is adapted to face away from the wearer during use. The disposable absorbent product also includes a pair of contoured edges defining respective leg openings of the absorbent product, each adapted to fit around a respective leg of the wearer. An absorbent core is disposed between the backsheet and the topsheet for absorbing and retaining fluid secreted by a wearer of the absorbent product. The absorbent core occupies a surface area equal to or greater than about 50% of the total surface area of the interior face.

In yet another embodiment, an absorbent core is provided for use with an absorbent product for absorbing and retaining fluid secreted by a wearer of the absorbent product. The absorbent core extends along a length dimension and a width dimension, and has a central portion, a pair of arm portions protruding longitudinally and laterally from the central portion, and a pair of leg portions protruding longitudinally and laterally from the central portion. The absorbent core may additionally have a terminal portion located centrally in the width dimension between the pairs of arm and leg portions, and protruding longitudinally from a remainder of the absorbent core.

In specific embodiments, the absorbent core also has a concave terminal edge located longitudinally opposite from the terminal portion and/or which extends between the leg portions. The absorbent core may additionally have a pair of concave lateral edges, each extending between one of the arm portions and one of the leg portions. Each of the leg portions in some embodiments of the absorbent core extends along a minor axis, with each of the minor axes being angled with respect to a longitudinal axis of the absorbent core.

The shape and relative dimensions of the different embodiments of the absorbent core described herein advantageously aid in the prevention, or at least reduction, in the incidence of leakage of fluid (e.g., urine) secreted by the wearer. The technical advantages related to the various features are described more fully below.

BRIEF DESCRIPTION OF THE DRAWINGS

The objectives and features of the invention will become more readily apparent from the following detailed description taken in conjunction with the accompanying drawings in which.

DETAILED DESCRIPTION

Figure 1:
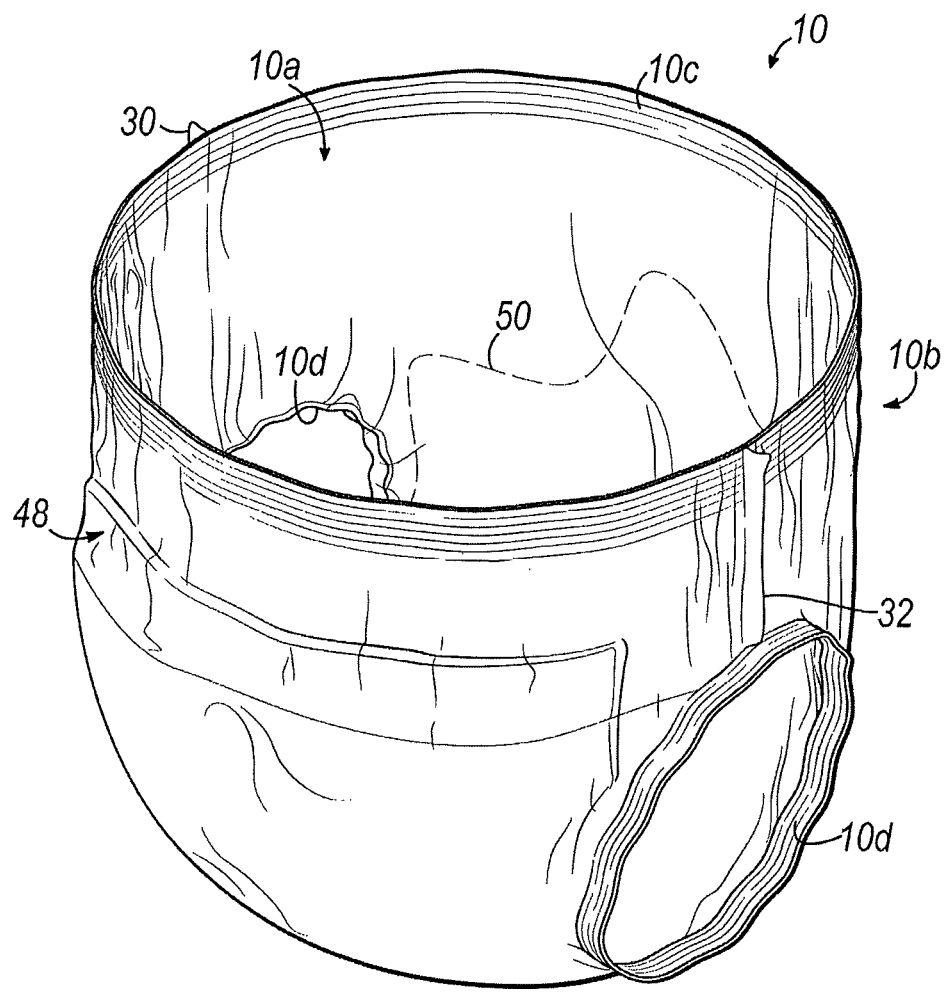
FIG. 1 is a perspective view of a disposable absorbent product in accordance with one embodiment of the invention.

With reference to the figures, and more particularly to FIGS. 1, 2, 3, 4A, 4B, and 4C, an exemplary disposable absorbent product in the form of a disposable pant 10, such as a training pant or an adult-size disposable pant, is illustrated. While these and other figures refer to a disposable pant, it is contemplated that the description herein and accompanying figures are applicable to other types of disposable absorbent products, and therefore not limited to disposable pants. The pant 10 is shown in its final, ready-to-use condition in FIG. 1, and shown in an open condition in FIG. 2, for illustration purposes. Pant 10 has an interior 10a that faces the body of the wearer (not shown), and an exterior 10b that faces away from the body of the wearer. A waist opening 10c, as well as a pair of leg openings 10d, jointly permit the mounting of pant 10 onto the body of the wearer, in ways known to those of ordinary skill in the art.

Figure 2:
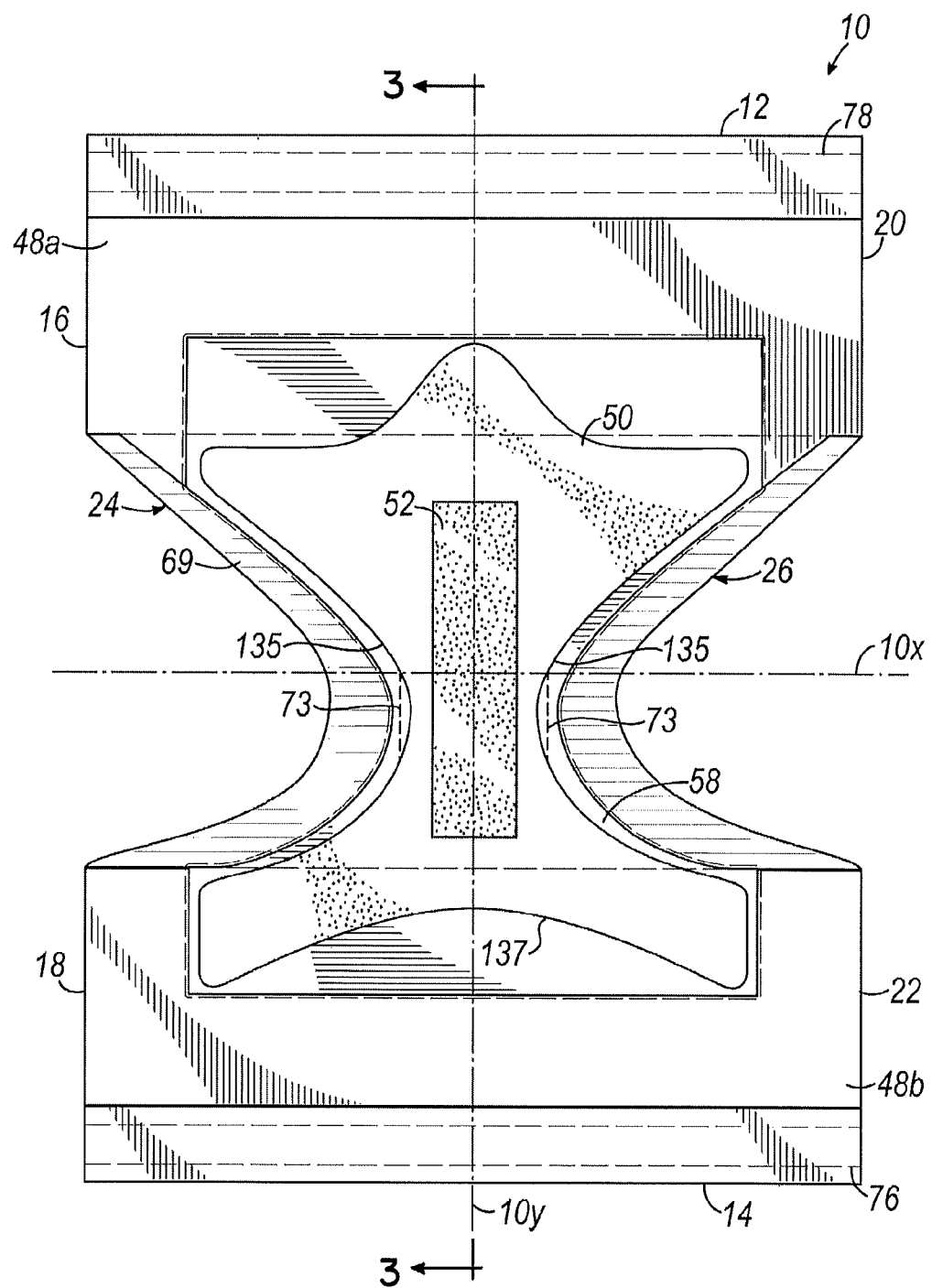
FIG. 2 is a top view of the disposable absorbent product of FIG. 1.

Referring particularly to FIG. 2, the pant 10 extends laterally (i.e., in the width dimension) along an orthogonal axis 10x and longitudinally along a longitudinal axis 10y. The perimeter of the pant 10 includes a pair of longitudinal ends 12, 14, a first pair of side edges 16, 18 on one side of the longitudinal axis 10y, and a second pair of side edges 20, 22 on the opposite side of longitudinal axis 10y. The perimeter of pant 10 also includes a first contoured leg opening 24 extending between the side edges 16, 18, and a second contoured leg opening 26 extending between the side edges 20, 22. As used herein, the term "contoured" refers to the generally curved shape of the leg openings 24, 26, designed to generally conform about the respective legs of the wearer. In this regard, contoured leg openings are contemplated having a single, continuous curve, as in the exemplary leg openings 24, 26 of the figures herein, or having other partially or entirely curved shapes. In the finished i.e., ready-to-use condition of the pant 10, the confronting side edges 16, 18 are integral with one another, as are the confronting side edges 20, 22, so as to define the closed pant 10 shown in FIG. 1. More specifically, the juncture of the side edges 16, 18 defines a first side seam 30 of pant 10, and the juncture of the side edges 20, 22 defines a second side seam 32.

Figure 3:
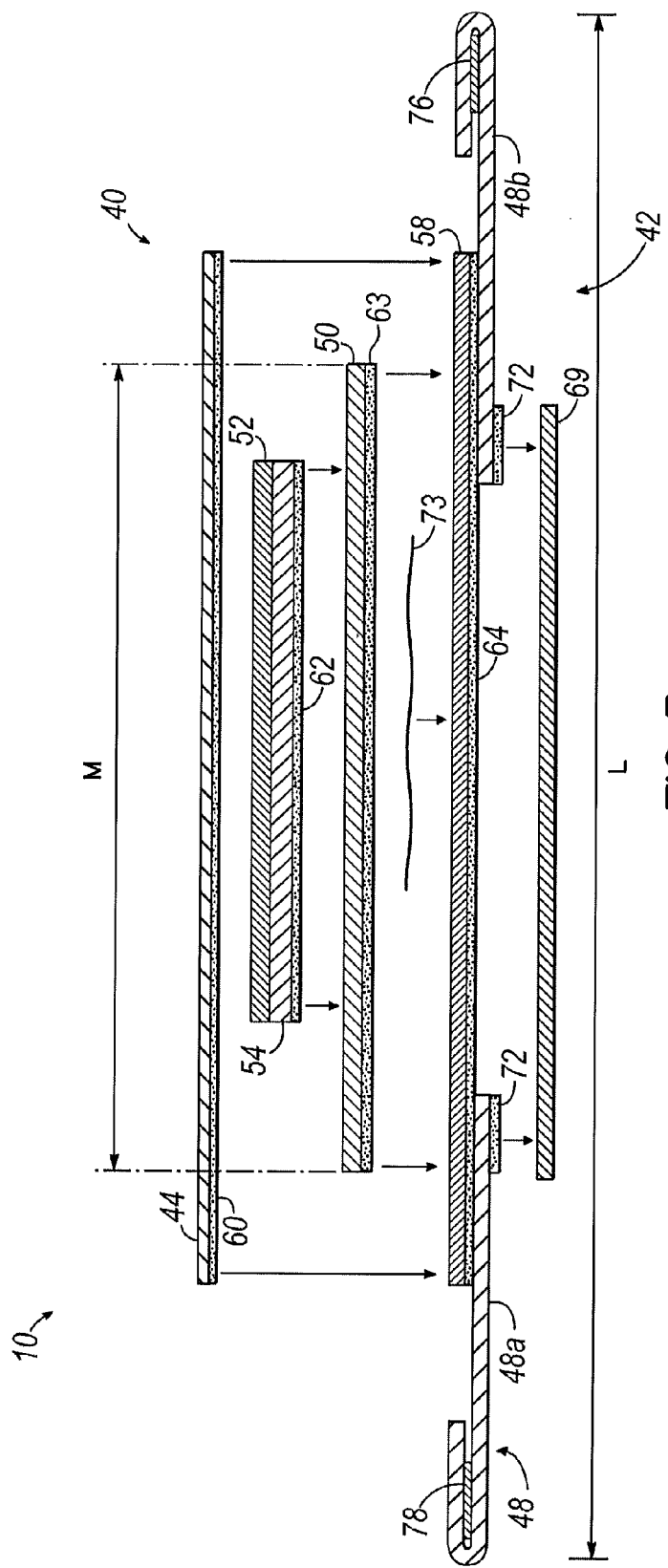
FIG. 3 is a cross-sectional, disassembled view along line 3-3 of FIG. 2.

Referring now particularly to FIG. 3, the pant 10 has an interior face 40 and an exterior face 42 respectively defining the interior 10a and exterior 10b of the pant 10 in its ready-to-use condition (FIG. 1). A topsheet 44, made of a permeable, hydrophilic nonwoven material defines at least a portion of the interior face 40. More specifically in the exemplary embodiment of FIG. 3, the topsheet 44 is a substrate layer longitudinally shorter than the overall length L of the pant 10. It is contemplated, however, that the topsheet 44 may instead have substantially the same length as the overall length L of the pant 10, or be even longer than the length L (i.e., folded at one or both longitudinal ends) and still fall within the scope of the present disclosure. A suitable topsheet material is a spunbond polypropylene ("SBPP") nonwoven commercially available from Polymer Group Inc ("PGI") of Charlotte, N.C. (USA).

An outer cover or backsheet 48, made of a hydrophobic material, defines at least a portion of the exterior face 42. More specifically in the exemplary embodiment of FIG. 3, the backsheet 48 is a substrate layer made up of two backsheet sections 48a, 48b, that are spaced from one another in the longitudinal direction. It is contemplated, however, that the backsheet 48 may alternatively be a single structure rather than having two or more separate structures, and still fall within the scope of the present disclosure. A material suitable for backsheet 48 is a breathable, high basis weight nonwoven, such as a spunbond/meltblown/spunbond ("SMS") polypropylene nonwoven commercially available under the designation S-S70-26 from Avgol Nonwoven Industries, of Tel-Aviv, Israel. As used herein, the term "breathable" refers to nonwoven fabrics having an air permeability of at least about 2800 l/m$^2$/sec under the WSP 70.1 test method (by Worldwide Strategic Partners). Also as used herein, the term "high basis weight" refers to nonwoven fabrics having a basis weight of at least about 10 g/m$^2$.

Pant 10 also includes an absorbent core 50, made of fluff pulp or a combination of fluff pulp or some other natural or synthetic fluid management material, and a fluid storage material such as superabsorbent material ("SAP") or some other natural or synthetic fluid storage material. The absorbent core 50 is positioned in pant 10 so as to extend along the same longitudinal axis 10y of the pant 10, and is located in the space between the topsheet 44 and backsheet 48, and is configured to absorb, distribute, and/or store bodily fluids e.g., urine, secreted by the wearer of the pant 10. Other absorption components may be present as well. In the embodiment illustrated in FIG. 3, for example, the pant 10 includes an acquisition layer 52 and an airlaid layer 54, both of which aid in the acquisition, distribution, and/or directing of fluid to the absorbent core 50. A suitable absorption component structure is an acquisition layer/airlaid layer composite commercially available from Glatfelter Falkenhagen GmbH, of Falkenhagen, Germany.

Other embodiments are also contemplated in which the pant 10 includes no additional absorption components or which includes only one such component rather than the two components described herein with respect to the embodiment of FIG. 3. The composition, shape and dimensions of each of any additional absorption components are suitably chosen. As seen in FIGS. 2, and 4A-4C, for example, each of the exemplary absorption components 52, 54 is generally rectangular and extends laterally and longitudinally to an extent less than the corresponding width and length dimensions of the absorbent core 50. Those of ordinary skill in the art will readily appreciate that the shapes and dimensions of the exemplary components 52, 54 can be different from those shown in the FIGS. 2 and 4A-4C, so long as they cooperate with the absorbing function of the absorbent core 50 in the management of fluids secreted by the wearer, particularly urine.

With continued reference to FIGS. 2, 3, and 4A-4C, the pant 10 also includes an impermeable barrier layer 58 made of polyethylene or polypropylene, for example, and located between the backsheet 48 and the absorbent core 50. In use, the barrier layer 58 prevents fluid from flowing from the absorbent core 50 to the backsheet 48, which in certain embodiments may be made of a permeable material, such as a cloth-like nonwoven material. The different components described herein are secured relative to one another in ways known to those of ordinary skill in the art. FIG. 3, in particular, illustrates various adhesive components, applied in a suitable chosen pattern, that secure the various layers making up pant 10. For example, adhesive component 60 secures the topsheet 44 to the acquisition layer 52 and to the barrier layer 58. Adhesive components 62 and 63 respectively secure the airlaid layer 54 to the absorbent core 50 and the absorbent core 50 to the barrier layer 58. An adhesive component 64 secures the barrier layer 58 to the backsheet portions 48a, 48b making up the backsheet 48, and to a multidirectional stretch material layer 69 adjacent the backsheet 48, that defines a portion of the exterior face 42 of pant 10. In addition, adhesive components 72 secure the longitudinal ends of the multidirectional stretch material layer 69 to the backsheet portions 48a, 48b. Other aspects of multidirectional stretch material layer 69 are explained more fully below.

While the above description and the figures refer to adhesive components securing different structural components (e.g., substrate layers) of the pant 10 to one another, these are intended to be exemplary rather than limiting. More specifically, it is contemplated that two or more of the structural components of pant 10 may instead or in addition be secured to one another mechanically, for example through ultrasonic bonding, CPW bonding, or heat bonding.

Figure 4A:
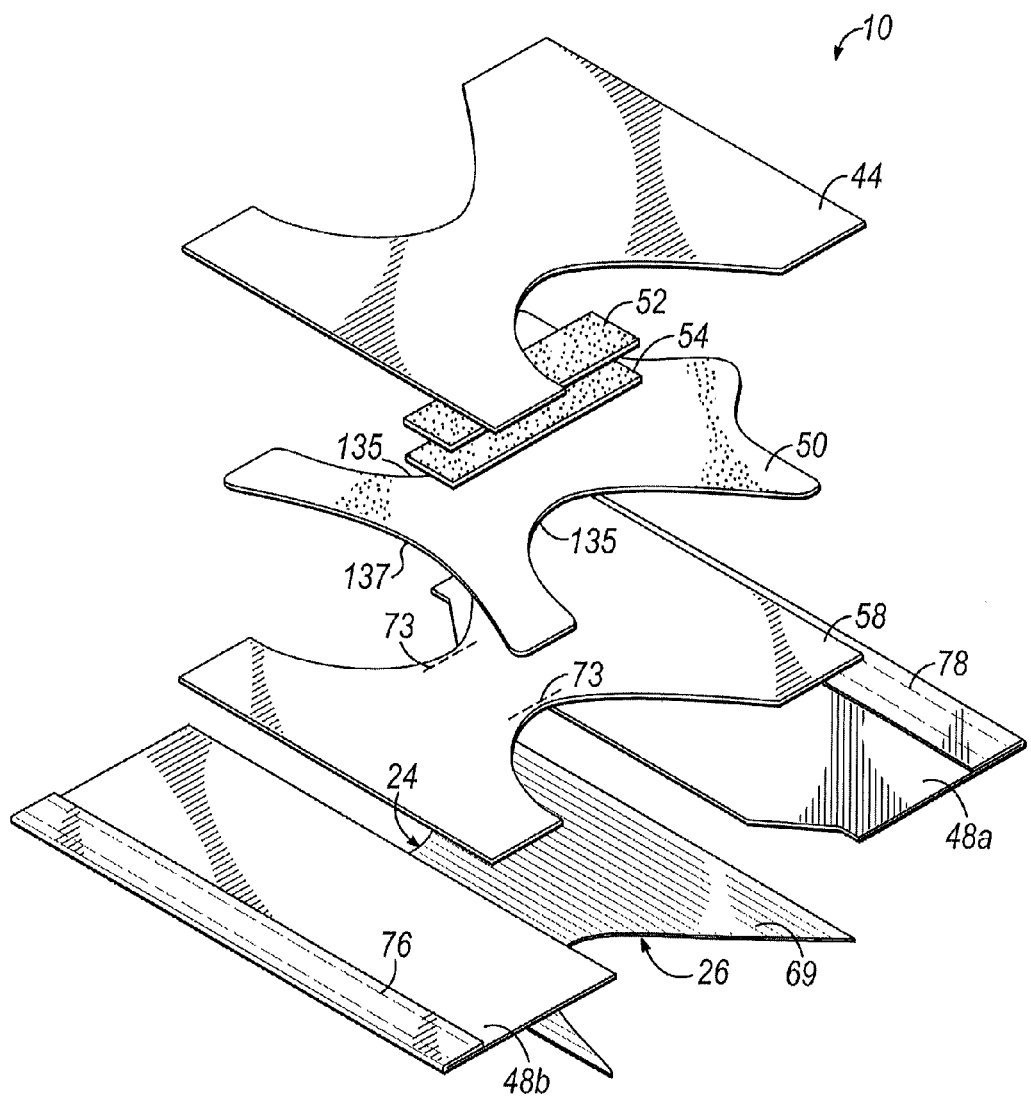
FIG. 4A is a disassembled view of the disposable absorbent product of FIGS. 1-3.
Figure 4B:
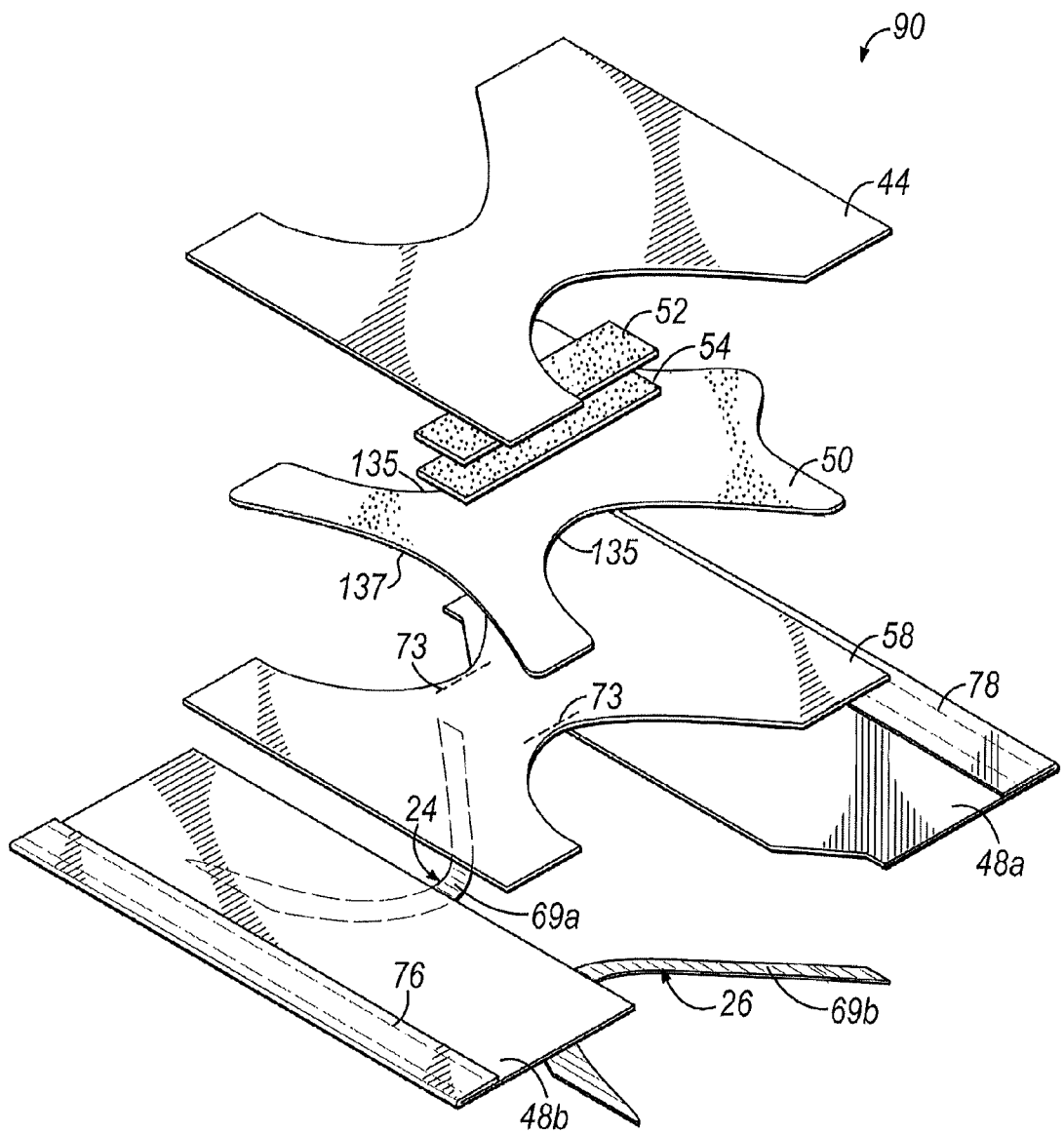
FIG. 4B is a view similar to FIG. 4A, illustrating a disposable absorbent product in accordance with another embodiment of the invention.

In the exemplary embodiment of FIGS. 2, 4A and 4B, each of the pants 10, 90 includes a pair of elastic strands 73, spaced laterally from one another, and secured against the front surface of the barrier layer 58 in a pre-stretched condition, so as to allow the pant 10, 90 to gather longitudinally in the crotch area when in the ready-to-use condition (FIG. 1). The elastic strands 73 are free of contact with the multidirectional stretch material layer 69, by virtue of being secured to the front surface of the barrier layer 58. The elastic strands 73 extend longitudinally a relatively short distance, and are substantially located only in the crotch area of the pant 10, 90. More specifically, the elastic strands 73 are shorter than the overall length L (FIG. 3) of the pant 10, 90 and also shorter than the length M (FIG. 3) of the absorbent core 50. In another aspect, the elastic strands 73 are located outboard of the central crotch portion of the absorbent core 50, as best seen in FIG. 2. The relative dimensions and location of the elastic strands 73 enhance the fit and comfort of the pant 10, 90 on the wearer, while also enhancing the prevention of leakage in the crotch area. A suitable type of elastic strands is Lycra® strands, commercially available from Invista North America, of Wichita, Kans. (USA).

Pant 10 also includes a pair of elastic bands 76, 78, located at the longitudinal ends of pant 10, and respectively defining the front and back waist regions. Each of the elastic bands 76, 78 is free of exposure to the wearer. More specifically, each of the elastic bands 76, 78 is encased by a respective folded-upon-itself portion at the longitudinal ends of the backsheet portions 48a, 48b. The elastic bands 48a, 48b may be made of natural or synthetic rubber or some other natural or synthetic material. Exemplary materials for the elastic bands are commercially available from Fulflex® Elastomerics Worldwide, of Brattleboro, Vt. (USA). The elastic bands 48a, 48b that are contemplated are generally flat structures, having a suitably chosen width that provides the pant 10 with an underwear-like appearance. In that regard, the elastic bands 48a, 48b may have a width, for example and without limitation, in the range of from about 10 mm to about 50 mm.

With particular reference to FIGS. 2 and 4A, the multidirectional stretch material layer 69 shown therein is a structure spanning across and defining both of the contoured leg openings 24, 26 of pant 10. In that regard, the lateral edges of the layer 69 are shaped so as to conform to the respective legs of the wearer. The multidirectional stretch material layer 69 is a hydrophobic material, having stretch characteristics in more than one direction, so as to more effectively conform to the legs of the wearer. The high level of conformance of the pant 10 around the legs of the wearer facilitates the prevention or at least reduction in the amount of fluid leakage observed with conventional disposable absorbent products. This contrasts with conventional disposable absorbent products having thin elastic strands at or near the leg openings, in which the leg openings stretch in only one direction by virtue of the elongation direction of the elastic strands.

The multidirectional stretch material layer 69 is secured to other portions of the pant 10, such as the backsheet portions 48a, 48b, in a pre-stretched (i.e., strained) condition. To that end, the material 69 may be stretched in one or more directions and secured, in that condition, to the backsheet portions 48a, 48b and/or to the barrier layer 58. An exemplary material suitable for the multidirectional stretch material layer 69 is a trilaminate commercially available under the trade name Flexaire™ 402, available from the Tredegar Corporation, of Richmond, Va. (USA). Other suitable materials include a nylon mesh or other materials capable of stretching in more than one direction to at least about 150% of the original dimension in the direction of the applied stretching force, and which can then retract to a dimension no greater than about 120% of the original dimension, in the direction of the applied stretching force. In specific embodiments, a multidirectional stretch material layer 69 is chosen having a color that is different from the rest of the pant 10, so as enhance the appeal of the pant 10 to the wearer and to provide a signal to the wearer of the presence of a multidirectional stretch feature in the pant 10.

Table 1, below, sets forth force vs. elongation data, in two directions orthogonal to one another, for an exemplary nylon mesh material that has been found to be suitable for the layer 69 of multidirectional stretch material described herein.

TABLE 1

Force vs. Elongation for Nylon Mesh

| % Elongation | Load (N) First Direction | Load (N) Second Direction |
| --- | --- | --- |
| 25 | 0.14 | 0.10 |
| 50 | 0.23 | 0.18 |

TABLE 1-continued

Force vs. Elongation for Nylon Mesh

| % Elongation | Load (N) First Direction | Load (N) Second Direction |
|---|---|---|
| 75 | 0.30 | 0.27 |
| 100 | 0.39 | 0.36 |
| 125 | 0.47 | 0.45 |
| 150 | 0.54 | 0.53 |
| 175 | 0.60 | 0.62 |
| 200 | 0.67 | 0.70 |

As table 1 above shows, an exemplary multidirectional stretch material suitable for the layer 69 is capable of stretching in either direction by 100% under an applied stretching force of about 0.36 to about 0.39 N. Similarly this exemplary material is capable of stretching in either direction by 150% under an applied stretching force of about 0.53 to about 0.54 N, and capable of stretching by 200% under an applied stretching force of about 0.67 to about 0.70 N.

FIG. 4B illustrates a different embodiment of a pant 90, similar in most respects to the pant 10 of the preceding figures. For ease of understanding, like reference numerals in FIG. 4B refer to similar features in the preceding figures. Pant 90 includes two multidirectional stretch material layers 69a, 69b, secured to both backsheet portions 48a, 48b and to the barrier layer 58, and spaced from one another in the lateral direction i.e., along the width dimension. The multidirectional stretch material layer 69a defines the contoured leg opening 24, while the other multidirectional stretch material layer 69b defines the other contoured leg opening 26. This embodiment is configured to use less multidirectional stretch material than the embodiment of FIG. 4A, which may be desirable.

Figure 4C:
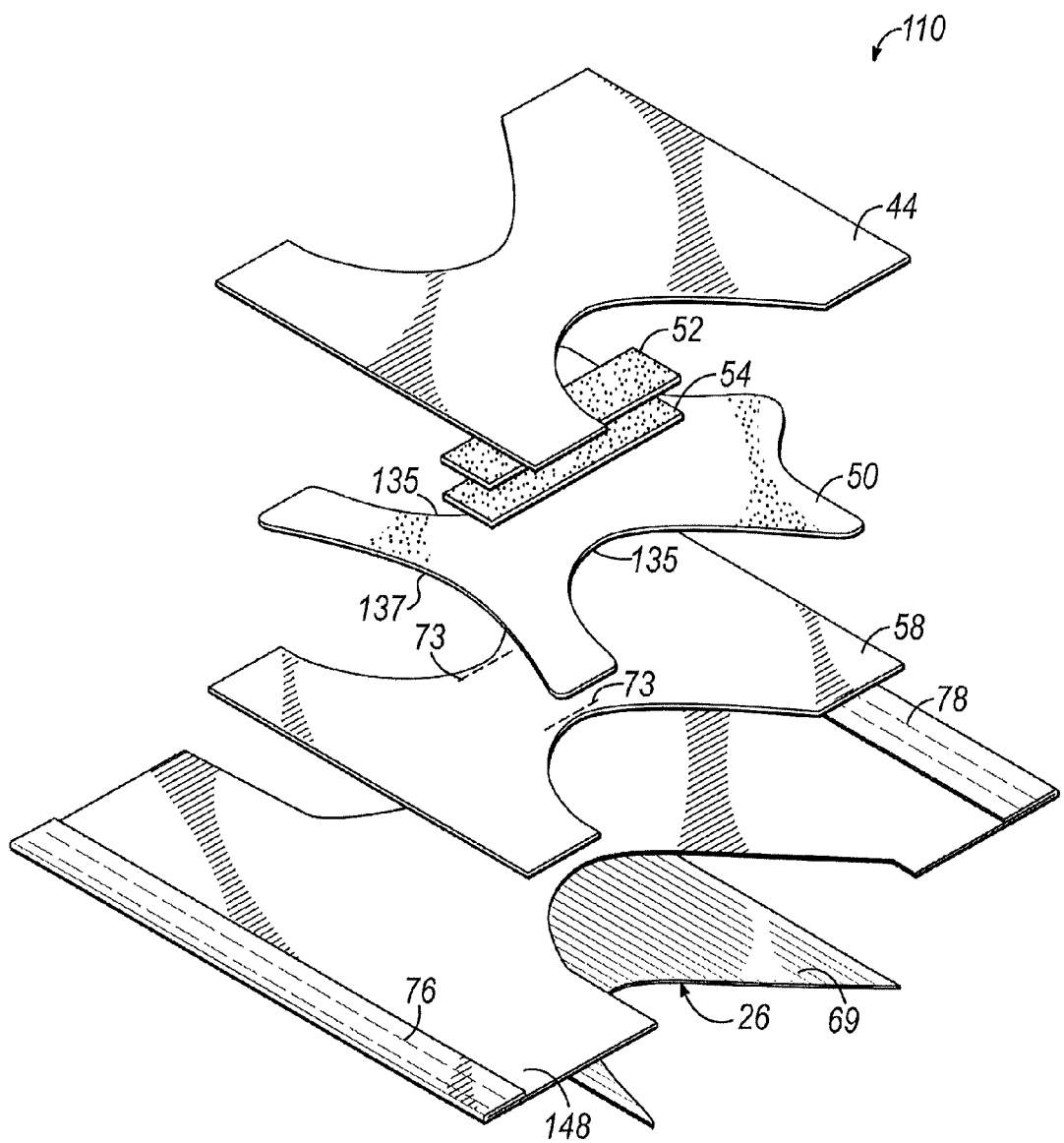
FIG. 4C is a view similar to FIG. 4A, illustrating a disposable absorbent product in accordance with yet another embodiment of the invention
Figure 5:
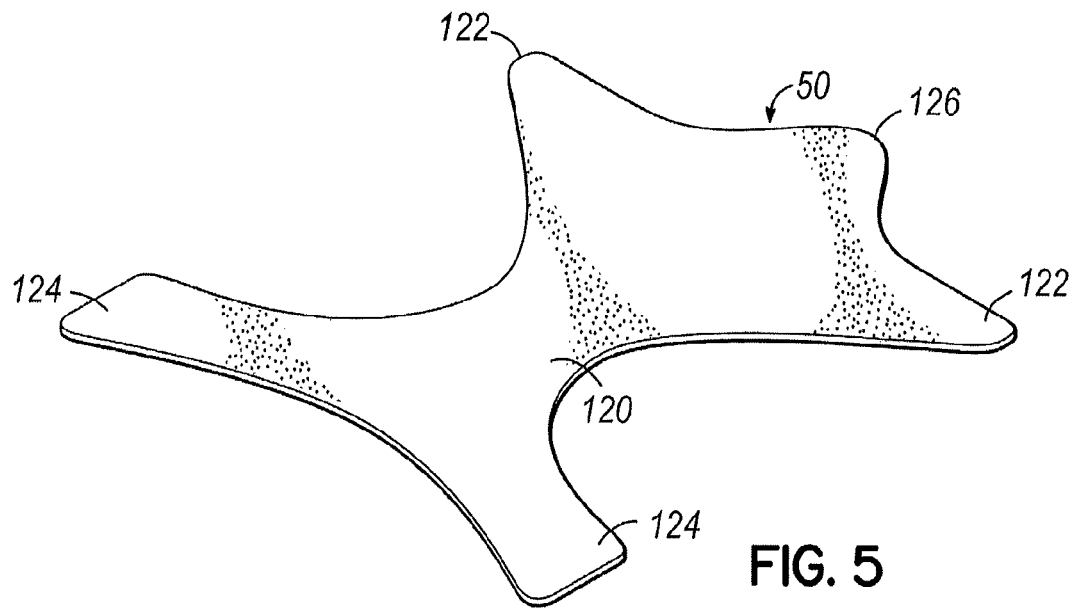
FIG. 5 is a perspective view of an absorbent core forming part of the disposable absorbent product of FIG. 1-3, 4A, 4B, or 4C.
Figure 6:
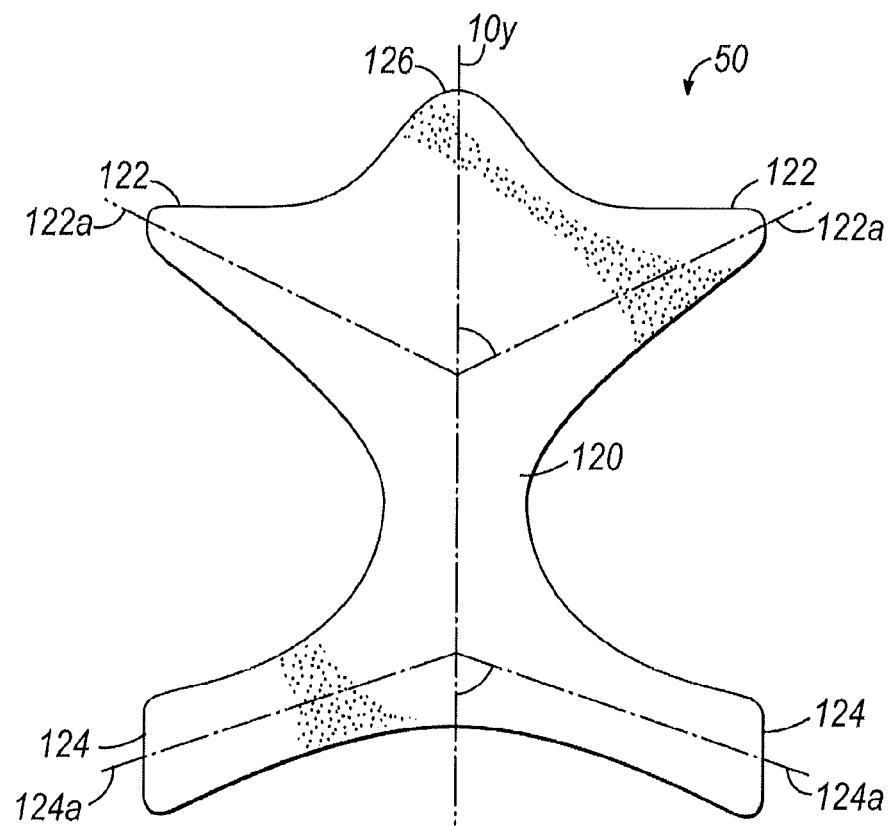
FIG. 6 is a top view of the absorbent core of FIG. 5.
Figure 7:
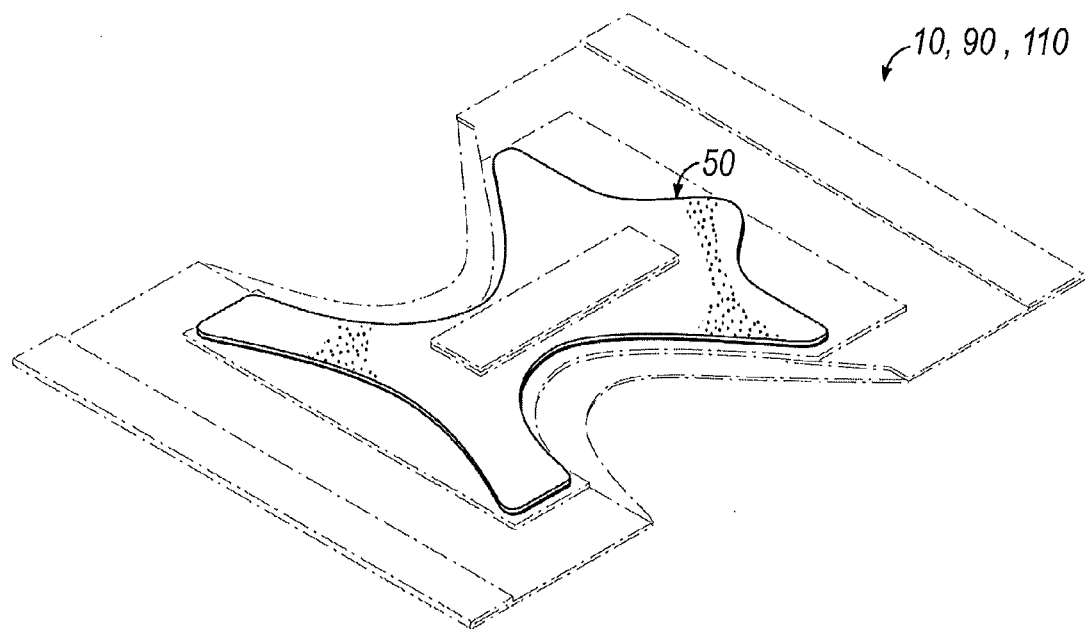
FIG. 7 is another perspective view of the absorbent core of FIG. 5, illustrating, in phantom, other exemplary structural elements of a disposable absorbent product of which the absorbent core forms part.

Referring now to FIG. 4C, that figure illustrates an embodiment of a pant 110 similar to the pant 10 of FIG. 4A. For ease of understanding, like reference numerals in FIG. 4C refer to similar features in the other figures. Pant 110 has a single-structure backsheet 148, spanning the entire length of the pant 110. This contrasts with pant 10 of FIG. 4A, in which the backsheet 48 is made up of two longitudinally-spaced backsheet portions 48a, 48b. The embodiment of FIG. 4A is configured to use less backsheet material than the embodiment of FIG. 4A, which may be desirable.

Referring particularly to FIGS. 2, 4A-4C, and 5-7, the absorbent core 50 is designed to maximize the absorbent capacity of the pant 10, 90, 110, and to prevent or at least reduce leakage of fluid e.g., urine, secreted by the wearer. More specifically, the absorbent core 50 is a symmetrical structure having a central portion 120, a pair of arm portions 122 extending along respective minor axes 122a, and a pair of leg portions 124 extending along respective minor axes 124a. Each of a pair of concave, arcuate lateral edges 135 of absorbent core 50 match respective ones of the leg openings 24, 26, as best seen in FIG. 2, with each of those lateral edges 135 being located entirely on one side of the longitudinal axis 10y, and extending between one of the arm portions 122 and one of the leg portions 124. The orientation of each of the arm and leg portions 122, 124 is such that each protrudes laterally and longitudinally from the central portion 120. In that regard, each of the respective minor axes 122a, 124a is angled i.e., it defines an acute or obtuse angle relative to the longitudinal axis 10y of the pant 10, 90, 110. In the illustrated embodiment, moreover, the leg portions 124 are proximate the front waist portion of the pant 10, 90, 110 i.e., the region of the pant 10, 90, 110 that is intended, in use, to face the front waist of the wearer. Further in this embodiment, the arm portions 122 are proximate the back waist portion of the pant 10, 90, 110 i.e., the region of the pant 10, 90, 110 that is intended, in use, to face the back waist of the wearer.

The exemplary absorbent core 50 further includes a terminal portion 126 protruding longitudinally from a remainder of the absorbent core 50 and located centrally in the width dimension between the arm portions 122. Notably in this embodiment, the terminal portion 126 is located proximate the back waist portion of the pant 10, 90, 110, which prevents or at least reduces leakage of fluid through the back waist of the wearer. The illustrated embodiment also has a concave, arcuate terminal edge 137, located longitudinally opposite from the terminal portion 126, extending between the leg portions 124, and which is shaped so as to enhance comfort and fit on the wearer. While not shown, other embodiments are contemplated additionally or alternatively having another protruding terminal portion, similar to terminal portion 126, extending longitudinally from the remainder of the absorbent core 50, but located in the front waist portion of the pant 10, 90, 110 i.e., in place of the concave terminal edge 137 of the exemplary absorbent core 50. In those alternative embodiments, the protruding terminal portion (not shown) in the front waist portion of the pant 10, 90, 110 enhances the prevention or reduction of leakage through the front waist of the wearer, which may be especially desirable for male wearers.

With continued particular reference to FIGS. 2, 4A-4C, and 5-7, the arm and leg portions 122, 124 extend the coverage of the absorbent core along the leg openings 24, 26, which enhances the prevention or at least the reduction of leakage of fluid (e.g., urine) secreted by the wearer through areas adjacent the legs of the wearer. And as discussed above, the multidirectional stretch layer(s) of the pant 10, 90, 110 also enhances the protection against leakage. In this regard, the high level of conformance of the multidirectional stretch layer(s) to the legs of the wearer prevent the escape of fluid along the surfaces of the legs of the wearer, while the relatively large coverage of absorbent core 50 adjacent the leg openings 24, 26 allows the pant 10, 90, 110 to absorb fluid that would otherwise tend to leak. The large coverage provided by the absorbent core 50 in specific embodiments is such that the ratio of surface area of the absorbent core to the total surface area of the pant 10, 90, 110, measured as the pant 10, 90, 110 is in the open condition (FIGS. 2 and 7), is of at least about 50%. In certain embodiments, that ratio is greater than about 55%.

While the above description refers to an absorbent core 50 that forms part of a disposable absorbent product such as pant 10, 90, 110, it is contemplated that the structures described therein can be used to manufacture only absorbent cores, rather than full disposable absorbent products. More specifically, embodiments are contemplated consisting of a core insert manufactured in one location and which is then supplied to another manufacturing location or to a consumer, in the form of an absorbent core insert, to be used with a disposable absorbent product or even with a non-disposable absorbent product (e.g., underwear or brief).

Figure 8:
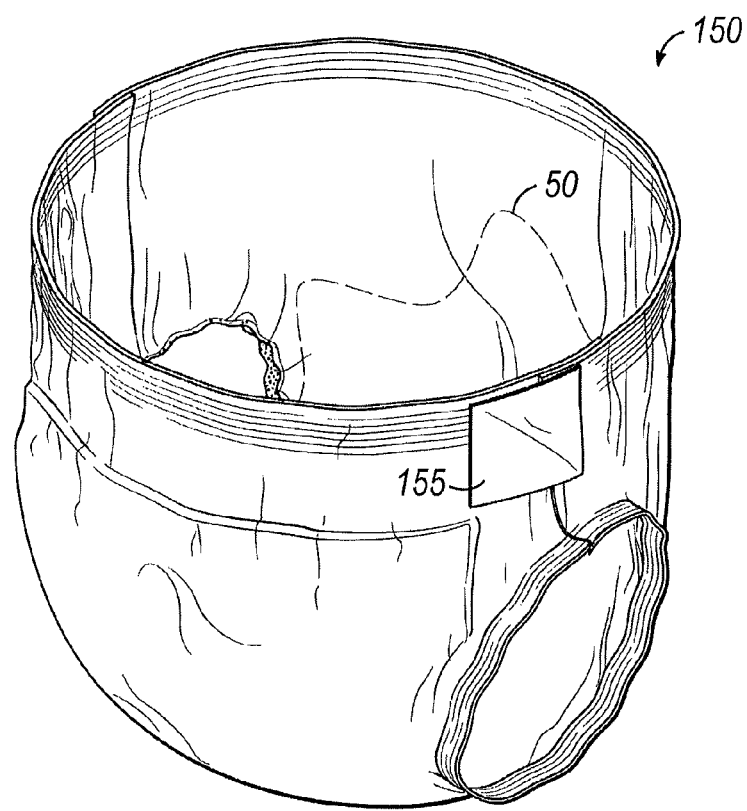
FIG. 8 is a perspective view of a disposable absorbent product in accordance with another embodiment of the invention.

Referring now to FIG. 8, that figure illustrates another exemplary embodiment of a disposable absorbent product in the form of an open diaper or brief 150. For ease of understanding, like reference numerals in FIG. 6 refer to similar features in the preceding figures, the details and description of which may be referred to as well for an understanding of the structure and functionality of diaper 150. In diaper 150, the front and back portions thereof are secured to one another on the wearer through a fastening component, such as an adhesive or hook-and-loop type fastener 155, that can be secured directly onto the outer surface of the backsheet 48, or alternatively secured to a "landing zone" (not shown) feature that is in turn attached to the backsheet 48. Other features of diaper 150 are similar in most respects to the various features described above with respect to the embodiments of FIGS. 1-3, 4A-4C, and 5.

From the above disclosure of the general principles of the present invention and the preceding detailed description of exemplary embodiments, those skilled in the art will readily comprehend the various modifications to which this invention is susceptible. Accordingly, this invention is intended to be limited only by the scope of the following claims and equivalents thereof.

What is claimed is:

1. A disposable absorbent product extending along a longitudinal axis defining a longitudinal dimension of the absorbent product, and along a transverse axis defining a width dimension of the absorbent product, the absorbent product comprising:
   a first longitudinal end defining a front waist portion of the absorbent product adapted to face the front waist of a wearer of the absorbent product when the absorbent product is worn by the wearer;
   a second longitudinal end, opposite said first longitudinal end, and defining a back waist portion of the absorbent product adapted to face the back waist of the wearer of the absorbent product when the absorbent product is worn by the wearer;
   a backsheet extending between said first and second longitudinal ends;
   a topsheet overlaying said backsheet; and
   an absorbent core disposed between said backsheet and said topsheet for absorbing and retaining fluid secreted by the wearer of the absorbent product, said absorbent core including a pair of arm portions, a pair of leg portions longitudinally opposed from said pair of arm portions, and a terminal portion located centrally in the width dimension between said pair of arm portions and extending longitudinally to a greater extent than all other portions of said absorbent core, said terminal portion having a distally located first arcuate edge that is concave as viewed from a central portion of said absorbent core, said absorbent core further including a second arcuate edge located centrally in the width dimension between said pair of leg portions, and each of said leg portions being an elongate structure extending along a respective axis defining an acute angle with the longitudinal axis of the absorbent product,
   wherein:
      said distally located first arcuate edge is located adjacent and spaced from said second longitudinal end,
      said second arcuate edge is located adjacent and spaced from said first longitudinal end, and
      said second arcuate edge has a width that is greater than a width of said distally located first arcuate edge.

2. The disposable absorbent product of claim 1, wherein:
   said topsheet and backsheet jointly define an interior face of the disposable absorbent product adapted to face the body of the wearer when the absorbent product is worn by the wearer, and an exterior face thereof adapted to face away from the wearer when the absorbent product is worn by the wearer,
   said interior face has a total surface area, and
   said absorbent core occupies a surface area equal to or greater than about 50% of said total surface area of said interior face.

3. The disposable absorbent product of claim 1, wherein said absorbent core includes a pair of centrally located lateral edges that are convex as viewed from said central portion and each extending between one of said arm portions and one of said leg portions, and wherein said second arcuate edge is convex as viewed from said central portion.

4. The disposable absorbent product of claim 1, further comprising a pair of contoured edges defining respective leg openings of the absorbent product, each adapted to fit around a respective leg of the wearer, said absorbent core including a pair of lateral edges each shaped so as to generally match the shape of an adjacent one of said contoured edges defining said leg openings.

5. The disposable absorbent product of claim 1, wherein a shape of said absorbent core resembles a five-point star.

6. The disposable absorbent product of claim 1, wherein said central portion, said pair of arm portions, said pair of leg portions, and said terminal portion form part of the same layer of said absorbent core.

7. The disposable absorbent product of claim 6, wherein said absorbent core includes an additional layer overlaying said layer that includes said central portion, said pair of arm portions, said pair of leg portions, and said terminal portion.

8. The disposable absorbent product of claim 1, wherein each of said leg portions includes a lateral edge that is generally parallel to the longitudinal axis of the absorbent product.

9. The disposable absorbent product of claim 8, wherein said absorbent core includes a pair of centrally located lateral edges that are convex as viewed from said central portion, each extending from the lateral edge of a respective one of said leg portions to a respective one of said arm portions.

10. An absorbent core for placement between a topsheet and a backsheet of an absorbent product for absorbing and retaining fluid secreted by a wearer of the absorbent product, the absorbent core extending along a longitudinal axis defining a length dimension of the absorbent core, and along a transverse axis defining a width dimension of the absorbent core, comprising:
   a central portion;
   a pair of arm portions protruding longitudinally and laterally from said central portion;
   a pair of leg portions protruding longitudinally and laterally from said central portion and disposed longitudinally opposed from said pair of arm portions;
   a terminal portion located centrally in the width dimension between said pair of arm portions, extending longitudinally to a greater extent than all other portions of the absorbent core, and including a distally located first arcuate edge, said distally located first arcuate edge being concave as viewed from said central portion; and
   a second arcuate edge located centrally in the width dimension between said pair of leg portions, each of said leg portions being an elongate structure extending along a respective axis defining an acute angle with the longitudinal axis of the absorbent core,
   wherein:
      said second arcuate edge has a width that is greater than a width of said distally located first arcuate edge and is convex as viewed from said central portion,
      each of said leg portions includes a lateral edge generally parallel to the longitudinal axis of the absorbent core, and
      said second arcuate edge includes a continuous curve extending from the lateral edge of one of said leg portions to the lateral edge of the other of said leg portions.

11. The absorbent core of claim 10, further comprising:
a pair of centrally located lateral edges, each extending between one of said arm portions and one of said leg portions, said lateral edges being convex as viewed from said central portion.

12. The absorbent core of claim 11, wherein each of said pair of centrally located lateral edges extends from the lateral edge of a respective one of said leg portions to a respective one of said arm portions.

13. The absorbent core of claim 10, wherein a shape of said absorbent core resembles a five-point star.

14. The absorbent core of claim 10, wherein said central portion, said pair of arm portions, said pair of leg portions, and said terminal portion form part of the same layer of the absorbent core.

15. The absorbent core of claim 14, further comprising an additional layer overlaying said layer that includes said central portion, said pair of arm portions, said pair of leg portions, and said terminal portion.

16. The absorbent core of claim 10, wherein the absorbent core is configured for use with an absorbent product for absorbing and retaining fluid secreted by a wearer of the absorbent product.

17. The absorbent core of claim 10, wherein said second arcuate edge includes a continuous curve extending from the lateral edge of one of said leg portions to the lateral edge of the other of said leg portions.

18. A disposable absorbent product extending along a longitudinal axis defining a longitudinal dimension of the absorbent product, and along a transverse axis defining a width dimension of the absorbent product, the absorbent product comprising:
a first longitudinal end defining a front waist portion of the absorbent product adapted to face the front waist of a wearer of the absorbent product when the absorbent product is worn by the wearer;
a second longitudinal end, opposite said first longitudinal end, and defining a back waist portion of the absorbent product adapted to face the back waist of the wearer of the absorbent product when the absorbent product is worn by the wearer;
a backsheet;
a topsheet overlaying said backsheet; and
an absorbent core disposed between said backsheet and said topsheet for absorbing and retaining fluid secreted by the wearer of the absorbent product, said absorbent core including a pair of arm portions, a pair of leg portions longitudinally opposed from said pair of arm portions, a pair of lateral edges convex as viewed from a central portion of said absorbent core and each extending between a respective one of said arm portions and a respective one of said leg portions, and a terminal portion located centrally in the width dimension between said pair of arm portions and extending longitudinally to a greater extent than all other portions of said absorbent core, said terminal portion having a distally located first arcuate edge, said distally located first arcuate edge being concave as viewed from said central portion of said absorbent core, said absorbent core further including a second arcuate edge located centrally in the width dimension between said pair of leg portions, and each of said leg portions being an elongate structure extending along a respective axis defining an acute angle with the longitudinal axis of the absorbent product,
wherein:
said distally located first arcuate edge is located adjacent and spaced from said second longitudinal end,
said second arcuate edge is located adjacent and spaced from said first longitudinal end,
said second arcuate edge has a width that is greater than a width of said distally located first arcuate edge and is convex as viewed from said central portion,
said central portion, said pair of arm portions, said pair of leg portions, and said terminal portion form part of the same layer of said absorbent core,
each of said leg portions includes a lateral edge generally parallel to the longitudinal axis of absorbent product, and
said second arcuate edge includes a continuous curve extending from the lateral edge of one of said leg portions to the lateral edge of the other of said leg portions.

* * * * *